United States Patent
Rieser

(10) Patent No.: US 6,544,457 B1
(45) Date of Patent: Apr. 8, 2003

(54) HIGH SPEED INJECTION MOLDING APPARATUS AND METHOD FOR DENTAL FLOSS HOLDER

(75) Inventor: Alan J. Rieser, Charlton, MA (US)

(73) Assignee: Placontrol, Inc., San Diego, CA (US)

( * ) Notice: Subject to any disclaimer, the term of this patent is extended or adjusted under 35 U.S.C. 154(b) by 0 days.

(21) Appl. No.: 09/506,311

(22) Filed: Feb. 17, 2000

(51) Int. Cl.[7] .......................... B29C 45/14; B29C 70/68
(52) U.S. Cl. ...................... 264/229; 264/251; 425/111; 425/121; 425/123; 425/126.1; 425/289
(58) Field of Search ................................. 425/111, 121, 425/123, 126.1, 289; 132/323; 264/229, 251

(56) References Cited

U.S. PATENT DOCUMENTS

| | | | | |
|---|---|---|---|---|
| 3,843,297 A | * | 10/1974 | Espinosa | 425/289 |
| 3,926,201 A | * | 12/1975 | Katz | 132/323 |
| 4,006,750 A | * | 2/1977 | Chodorow | 132/323 |
| 4,016,892 A | * | 4/1977 | Chodorow | 132/323 |
| 4,029,453 A | * | 6/1977 | Campion, Jr. | 425/126.1 |
| 5,086,792 A | * | 2/1992 | Chodorow | 132/323 |
| 5,167,753 A | * | 12/1992 | McCullough et al. | 132/323 |
| 5,246,021 A | * | 9/1993 | Katz | 132/323 |

FOREIGN PATENT DOCUMENTS

| | | | |
|---|---|---|---|
| GB | 629153 | * | 9/1949 |
| JP | 03047251 A | * | 2/1991 |
| JP | 08173243 A | * | 7/1996 |
| JP | 09276297 A | * | 10/1997 |
| JP | 09294753 A | * | 11/1997 |
| JP | 10080437 A | * | 3/1998 |

* cited by examiner

Primary Examiner—Robert Davis
(74) Attorney, Agent, or Firm—Amster, Rothstein and Ebenstein

(57) ABSTRACT

An injection molding apparatus for manufacturing dental floss holders has at least one strand of dental floss from a supply spool extended through the space between mating mold pieces and thereafter to a take-up device. From each injection stage of the molding cycle a rack of connected dental floss holders is produced. Tension of the floss is maintained from the upstream supply spool by a first tensioning device through the mold to the downstream end by the take-up device. During each injection cycle the take-up device engages another rack of molded parts and moves it to a downstream position where it is severed from the strand of floss while it maintains the tension in the floss upstream of the severed rack. This is achieved by the take-up device engaging at least two successive racks downstream of the mold and using the rack closest to the mold to maintain tension.

39 Claims, 8 Drawing Sheets

HIGH SPEED INJECTION MOLDING APPARATUS AND METHOD FOR DENTAL FLOSS HOLDER

BACKGROUND OF THE INVENTION

1. Field of the Invention

This invention is in the field of apparatus and methods for manufacturing dental floss holders with high volume injection molding machines which draw one or more continuous strands of dental floss from a supply to and through the mold so that the floss is molded in situ into the dental floss holders which are ejected while still attached to the floss extending both upstream and downstream of the mold. Typically, a multi-cavity mold is used with each strand of floss in the mold spanning a plurality of cavities. This invention further concerns improved efficiency in processing the molded flossers, securing the floss therein and packaging same.

2. Relevant Prior Art

| Patent No. | Inventor | Date |
|---|---|---|
| 4,006,750 | I. S. Chodorow | 02/08/77 |
| 4,016,892 | I. S. Chodorow | 02/08/77 |
| D 244,376 | I. S. Chodorow | 05/ /77 |
| D 250,214 | I. S. Chodorow | 11/07/78 |
| 5,086,792 | I. S. Chodorow | 02/11/92 |

3. Background

Disposable dental floss holders, also called "flossers", have become popular alternatives to using traditional long strands of dental floss wrapped about the user's fingers. These flossers are now produced in great numbers; however, because each of these devices is quite small and is discarded usually after one or a few uses, it can command only a small sale price. Consequently, a manufacturer must produce huge volumes in the millions in order to be economically profitable. Under these circumstances improved efficiency of manufacture is a most significant aspect for economic viability.

In this high volume manufacture there are many problems including properly positioning the floss in the mold, securing the floss in the holders, minimizing breakage of the continuous strand(s) of floss extending from the floss supply to the point of severing molded flossers from the supply floss, selecting suitable plastic for the handle for the floss with regard to molding temperatures, strength and fraying, and post-molding operations of breaking the holders from the central runner, separating the flossers from each other, securing the floss ends in the handles and finally packaging the holders with efficient mass production techniques.

The present invention concerns a number of problem areas in the manufacturing and packaging process. The first is minimizing breakage of the floss supply lines during molding while maintaining proper predetermined tension in the floss so that the floss in each finished flosser will be relatively straight and taut.

In known high volume injection molding machines for producing dental floss holders, an objective is to maintain the floss in tension while it is drawn into the mold, during molding, and subsequently as quickly as possible to move the ejected aggregate of molded flossers ("shot") out of the mold and to move the next segment of floss into the mold. Also, the shot transported downstream must be severed from the successively molded shots, all the while trying to maintain proper tension in the floss which traverses the mold.

In the above described procedure there are persistent serious problems. When the floss is not properly tensioned in the mold the resulting flossers may have sloppy slack floss, or worse, the floss may be positioned incorrectly in the mold and become damaged. If the floss breaks anywhere between the supply at the upstream end and the severing point at the downstream end, the entire machinery has to be stopped, cleaned up, and new floss fed through the stages and tension re-established.

Such "down time", if frequent, obviously will greatly diminish efficiency and possibly render the entire process unprofitable. For injection cycles as fast as four to six per minute, for example, breakage of the floss or non-constant tension is recognized as a major problem. The present invention provides a novel apparatus and technique for overcoming this problem.

After the injection molded "shots" or racks of, for example, twenty flossers attached to a central runner are produced, the high efficiency mass production must be maintained during the stages of severing the flossers from the central plastic runner and from each other and securing the floss ends in the holder. The present invention provides new apparatus and techniques for improving this efficiency also.

SUMMARY OF THE NEW INVENTION

The new invention is an apparatus ancillary to an injection molding machine, operable with a supply of one or more a continuous strands of dental floss, a supply of injection-moldable plastic, and a multi-cavity mold having mating parts moveable between open and closed positions, with said dental floss extending from said supply between the faces of and through and out of said mold. The molding machine in operation produces a shot of a plurality of dental floss holders molded in situ onto said floss every injection cycle, where every two adjacent shots comprises a set with one of said set being the downstream shot and the other the upstream shot until the upstream shot becomes the downstream shot of the next adjacent shot. This molding machine apparatus further includes (a) first tension means constantly applying a force to said floss upstream of said mold and in the upstream direction, (b) take-off means downstream of said mold engaged to said floss and maintaining tension in the downstream direction by intermittently pulling said floss in said downstream direction, after each injection and ejection phase and holding said floss from moving without pulling in any direction during said injection and ejection stage, and (c) severing means for severing the downstream shot from the upstream shot of each of said sets received by said take-off means while said upstream shot remains engaged to said take-off means and maintains said tension in said floss downstream of said mold.

The second principal phase of this high speed—high volume production process invention concerns taking the molded shots as seen in FIG. 9, each shot containing a plurality of dental floss holders still joined to a central runner, feeder runner and gate and joined to each other via the continuous strand of floss, and proceeding with the steps of separating the individual flossers from the central runner and from each other, securing the floss ends to the holder simultaneously with severing the floss joining adjacent flossers, and finally packaging the flossers either individually or in groups.

DETAILED DESCRIPTION OF THE DRAWINGS

DETAILED DESCRIPTION OF THE PREFERRED EMBODIMENTS

Figure 2:
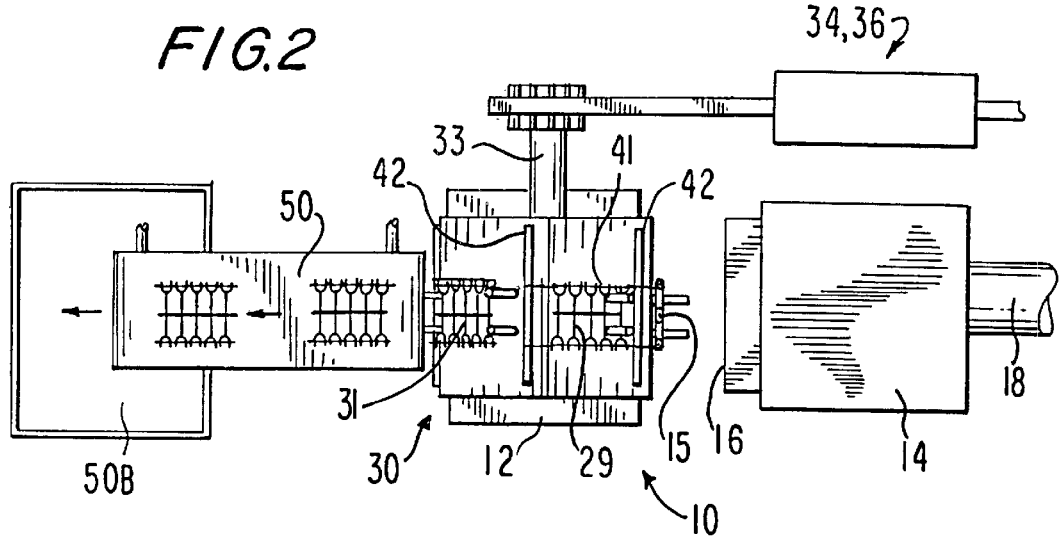
FIG. 2 is a top plan view of FIG. 1.
Figure 1:
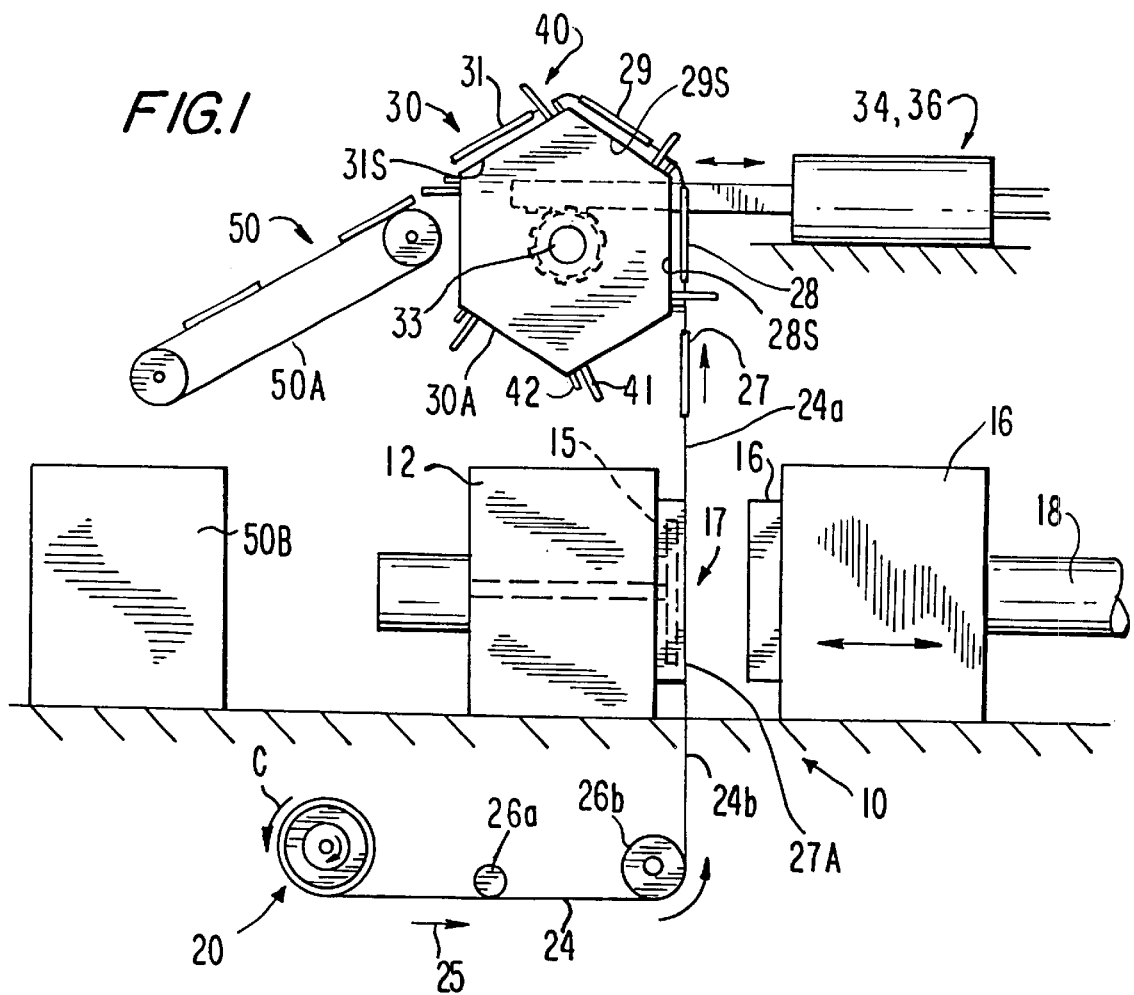
FIG. 1 is a schematic elevation view of the new invention.
Figure 3:
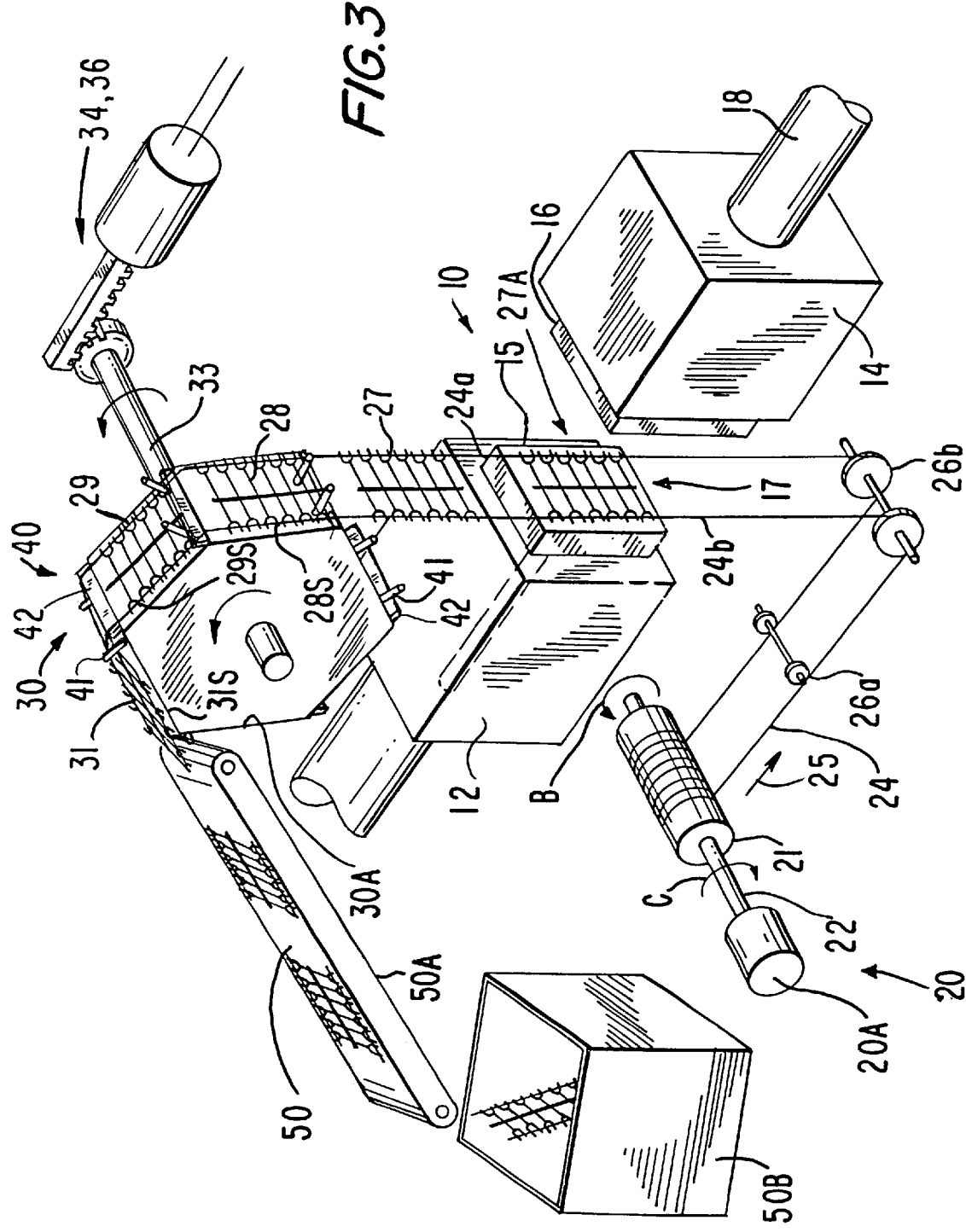
FIG. 3 is a perspective view of the apparatus of FIG. 1.
Figure 4:
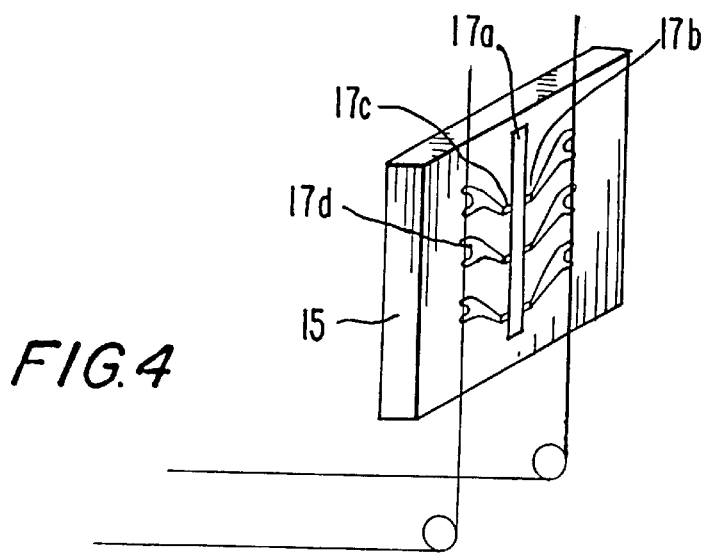
FIG. 4 is a fragmentary schematic view of a mold and the strand of floss traversing the cavities therein.

The injection molding machine and techniques of the new invention are illustrated in the drawings as described below. FIGS. 1–3 show schematically a basic injection molding machine as known in the prior art with a base 10, ejector housing 12 and mating housing 14, a two piece multi-cavity mold 15, 16. Raw plastic for the injection cycle is fed through inlet 18, the preferred plastic for the dental floss holders manufactured by this machine being polypropylene or polystyrene. The multi-cavity mold 15, 16 as seen in greater detail in FIG. 4 has cavities for the central runner 17a, feeder runners 17b, gates 17c and the principal flosser cavities 17d.

A supply of floss 20 is fed from spool (or cylinder or drum) 21 that rotates about central spindle 22. The wound floss 23 is a continuous strand of multifilamented ultra high molecular weight polyolefin, nylon or PTFE which reels off the drum 21 in a downstream direction indicated by arrow 25. Support rollers 26a, 26b guide and support the floss until it is directed to and through the mold 15, 16.

In the injection molding cycle, following injection and cooling, the mold opens and the shot or rack 27A of twenty injection molded flossers is ejected while they are still attached to and essentially suspended by the floss 24A above it (in the downstream direction) and floss 24b below it (in the upstream direction). More particularly the segment of floss 24a separates the shot 27A being ejected from the shot 27 previously ejected and moved upward when fresh floss was moved into space 17 between mating parts 15, 16 of the open mold. Above shot 27 are prior ejected shots 28 and 29 now engaged and pulled by the take-off mechanism 30 which is followed by the severing stage 40 and the discharge chute 50.

In the operation of this machine each time the molds 15, 16 opens and a shot is ejected, the take-off mechanism 40 pulls the floss and shots carried thereon one incremental distance corresponding to the length of one shot plus the length of floss between two adjacent shots. A brake mechanism 36 in or associated with the take-off drive 34 then stops and holds this new position where the floss and shots have been moved one unit of distance. A central timing control mechanism (not shown) then causes the mold to close, capturing a new segment or segments of floss to begin the next injection cycle.

A principal objective of this invention is to maintain a level of tension in the floss that extends through the open mold and upstream and downstream thereof
  (a) so that the floss when molded in situ into the floss holders will be generally uniformly taut and properly aligned within the mold, and
  (b) so that during the axial movement of the floss during the various phases of the molding cycle, excess tension will not develop causing breakage of the floss, and insufficient tension will not develop causing misalignment and/or tangling. Any of these problems causes an extremely costly shut-down of the entire apparatus until the interruption is cleared and restarted.

To achieve this constant but somewhat flexible level of tension in the floss, without stopping the process even while the most downstream shot is severed from the others for further processing, the new invention utilizes a new take-off structure in combination with magnetic clutch tensioning at the upstream supply end.

Figure 5:
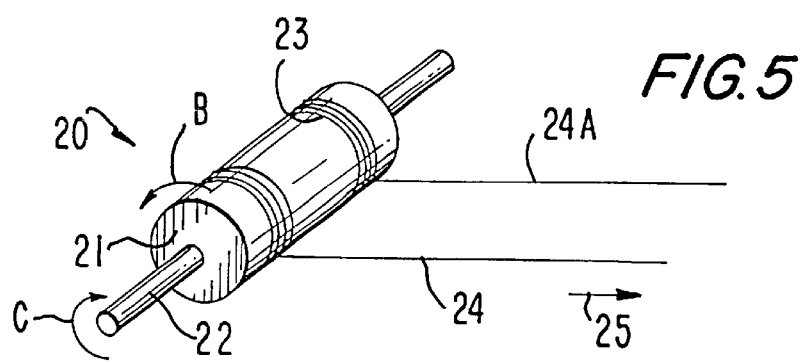
FIG. 5 is a schematic view of the supply drum of floss and magnetic clutch combination.
Figure 6:
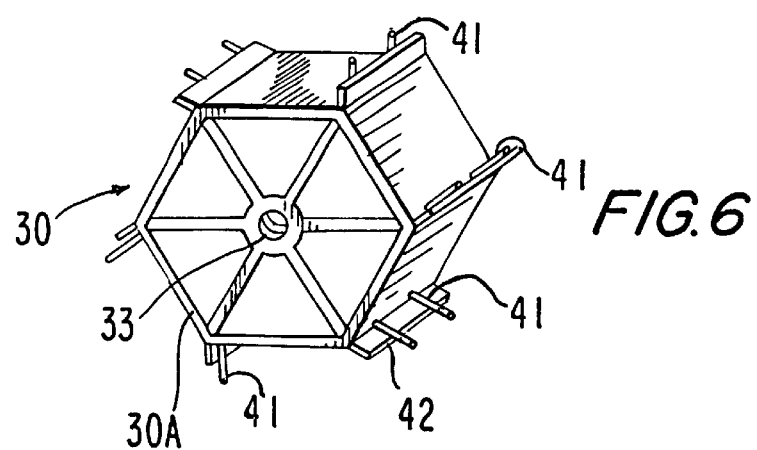
FIG. 6 is a schematic view of a take-off wheel and floss severing element.
Figure 7:
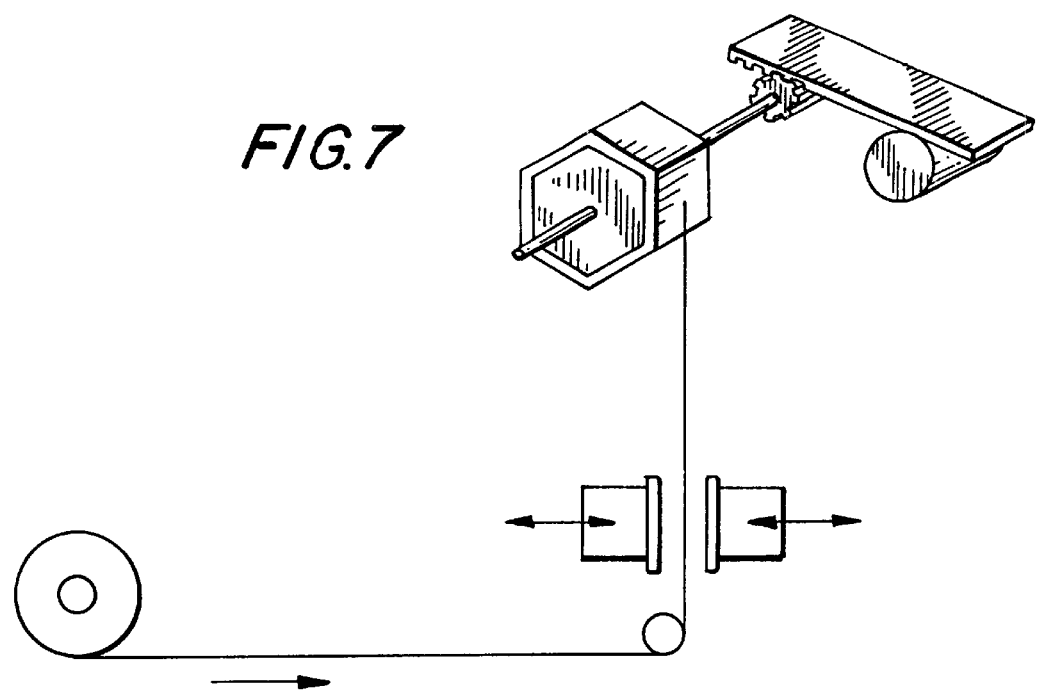
FIG. 7 is a schematic view showing the time and power coordinated elements, namely the floss supply tension, mold cycle, take-off wheel and burn phase.
Figure 8:
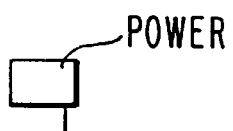
FIG. 8 is a schematic circuit diagram showing the operation of this invention.
Figure 8:
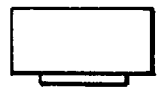
Figure 8:
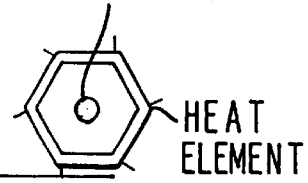

FIG. 5 shows schematically a known magnetic clutch 20 operable or incorporated with the cylindrical supply drum 21 carrying one or more continuous strands of floss 23. Spindle 22 is rotated clockwise per arrow C, from a known drive (20A seen in FIG. 3), and drum 21 is rotated counter clockwise per arrow B due to the pull on floss 24 in said downstream direction indicated by arrow 25.

A magnetic field is established between the spindle 22 and the drum 21 whereby rotation of the spindle in the direction opposite of the drum rotation tends to restrain the drum rotation and thus apply a tension on floss 24 in the upstream direction. This magnetic field is easily adjustable by means not shown to establish a specific or range of tension level applied to said floss. In this particular embodiment two separate strands of floss 24, 24A are unwinding from (reeling off) the supply drum 21 which is schematically representative of two separate spools or perns, since the mold of this embodiment is designed to receive two strands simultaneously. Typically the magnetic field will be set to apply a tension of about 10 pounds on the strands of floss. Because this force is applied by a magnetic field, it operates as a flexible force which is self-adjustable should the force on the floss become greater or smaller.

At the downstream end of the system are the take-off mechanism 30 and the severing station 40. Successive shots 27A, 27, 28 and 29 form a belt. As seen in FIGS. 1–3 shot 27A will be ejected from the mold, shot 27 has just been ejected and moved downstream toward the take-off wheel 30A, shot 28 has engaged side 28S of the wheel, shot 29 has engaged side 29S of the wheel and shot 31 is being severed from shot 29.

The take-off wheel 30A in FIGS. 1–3 and 6 has six equal surfaces about its outer periphery, thus defining hexagonal sides. The wheel is rotatable about a central axis 33 and is operated by a drive and control means 34, 36 which rotates the wheel in intermittent incremental steps of 60° each (⅙ of a revolution) and thus stops the wheel for the time period of the next injection cycle during which time the floss is captured in the mold and does not move axially. With each opening of the mold and ejection of the shot, the wheel 30A moves another 60° pulling the belt of shots one additional step downstream (and onto the wheel).

Should an unusually high tension develop in the upstream direction, the drive-brake-clutch arrangement 34, 36 for the wheel will release at about one hundred pounds to avoid breakage of the floss. Then the problem causing the excessive tension can be rectified and the system returned to normal operation.

Each of said six peripheral edge surfaces of wheel 30A has a shot-engagement means 41 formed as fingers projecting generally radially outward and adapted to hook beneath the bottom flossers in each shot as the shot comes to overlie said edge surface. By this engagement these fingers serve to apply a pulling force on the belt of shots extending upstream of the shot just engaged.

Further rotation of another 60° positions shot 29 at the top of the wheel while the next shot downstream becomes engaged by the next set of fingers of the next surface of the wheel. This engagement of each shot corresponding to 28 onto side 28A of the wheel is adequate to maintain the tension in the floss upstream of this engagement, such that the earlier engaged shot may be severed without affecting the tension maintained by shot 28 or its equivalent.

Consequently, at any time after the wheel 30A engages a new shot, the previously engaged shot could be severed. For this, the wheel could have six, or four or three or even two sides or engagement surfaces; however, the quantity of six forming a hexagon was chosen because of numerous practical benefits. With six sides, one side first receiving a shot can be easily aligned with the belt of shots emerging from the mold to readily receive same without changing its orientation. The shot essentially falls onto the wheel surface 28A and engagement by the fingers 41 is automatic. The next two 60° moves of the wheel reorient the shot to be severed into a suitable position to be dropped onto chute 50 which may be inclined to a receiving container 50B or may contain a conveyor belt 61 for transporting the severed shots to the next station. Two more 60° rotational movements of the wheel brings the now-exposed or empty side surface back into position to pick-up the next shot on the belt of shots.

The severing stage can be done in many ways including without limitation cutting and burning. In this embodiment a heat element 42 that burns the floss is positioned closely adjacent and upstream of said fingers 41 positioned just below the lowest of the flossers of the shot. At the appropriate time, namely, for example, when a set of adjacent downstream and upstream shots, 31, 29, respectively, are at the top of the wheel, and a further upstream shot is securely engaged to said wheel surface, the heat element is energized, thus severing shot 31 from shot 29, (a) without interrupting the maintenance of tension by the upstream shot 28, and (b) without altering or disturbing the structure or arrangement of flossers of the severed shot 31. The severed shot 31 then falls downward to the chute 50 or conveyor 50A where it is directed to the next stage.

The entire system has a central electronic control not shown to assure that the take-off wheel rotates each 60° step only after the mold is opened and the shot ejected, thus freeing the belt of shots and the entire proceeding (upstream) floss to move axially, subject only to the restraining force of the magnetic tensioning at the supply end and other normal frictional forces. Obviously, the timing control with drive/brake 34, 36 also stops the rotation after the 60° movement and holds this position until the injection, cooling and ejection phase is again completed. In this embodiment the cycle time is about 12 seconds between ejections. With a 20 cavity mold and a machine operating continuously, the production rate can be up to 144,000 per 24-hour day or 50.4 million per 50-week year. Such quantities cannot even be approached if the injection molding apparatus is continually stopped due to broken or tangled strands of floss. The present invention is highly effective in minimizing such problems.

Figure 9:
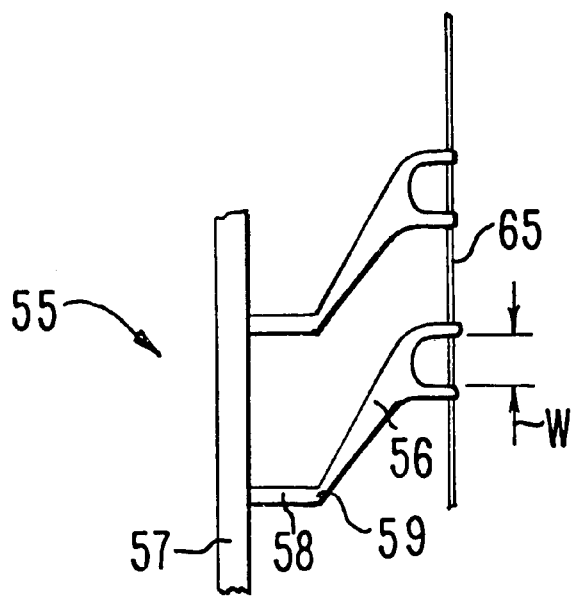
FIG. 9 is a fragmentary plan view showing a typical shot containing dental floss holders attached to a central runner.
Figure 10:
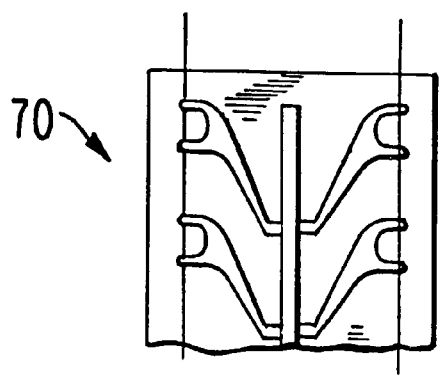
FIG. 10 is a detail view of a multi-cavity mold.

The second principal phase of this high speed—high volume production process invention concerns taking the molded shots as seen in FIG. 9, each shot 55 containing a plurality of dental floss holders 56 still joined to a central runner 57, feeder runner 58 and gate 59 and joined to each other via the continuous strand of floss 65, and proceeding with the steps of separating the individual flossers from the central runner and from each other, securing the floss ends to the holder simultaneously with severing the floss joining adjacent flossers, and finally packaging the flossers either individually or in groups.

Figure 11:
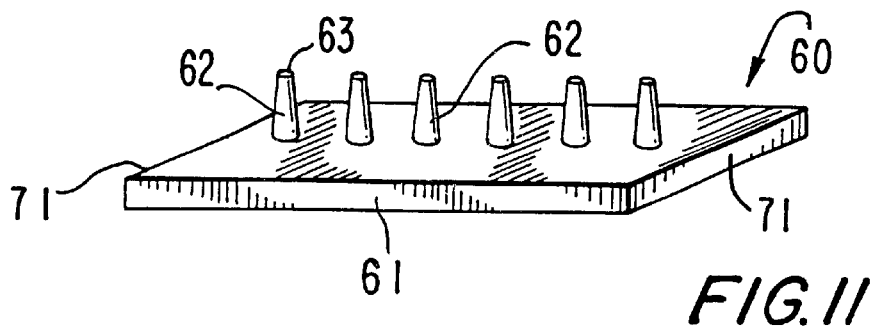
FIG. 11 is a perspective schematic view of a break-off fixture.
Figure 12:
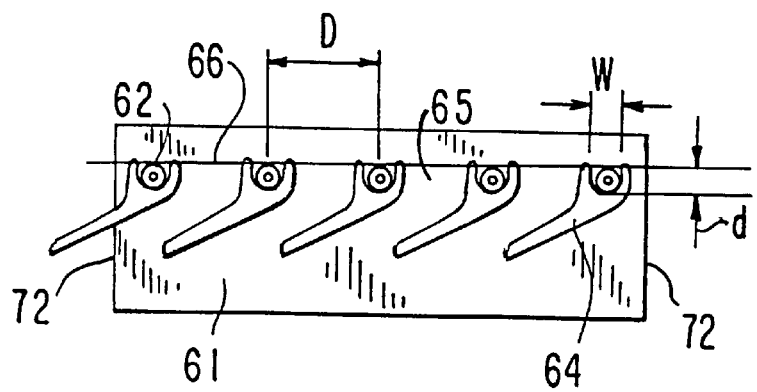
FIG. 12 is a top plan view of the break-off fixture of FIG. 11 with a shot of flossers positioned thereon.

FIG. 11 shows a break-off fixture 60 having a base 61 and a plurality of ten posts 62 tapered slightly from the bottom up and terminating in an axial aperture 63. As seen in FIG. 12 these posts are spaced apart a distance D the same as said flossers 64 are spaced in the shot of FIG. 9, and the base diameter width W of each post corresponds to the space between the pair of arms of each flosser. The base depth d of each post is essentially the same as the distance in each flosser from the floss to the yoke or arch joining the two arms.

After the shot is engaged on the fixture, the central runner 57, feeder runners 58 and gates 59 are broken off manually from the alignment of floss holders, with the remaining sub-assembly of holders joined only by the common strand of floss 65. This sub-assembly is positioned to overlie fixture 71 with the posts 62 protruding through the spaces between the pairs of arms respectively of the ten flossers. The floss 65 runs through the arms of adjacent flossers and extends as floss segments 66 (See FIG. 14c) between each two adjacent flossers. A multitude of shots is similarly stacked on the fixture.

Figure 14A:
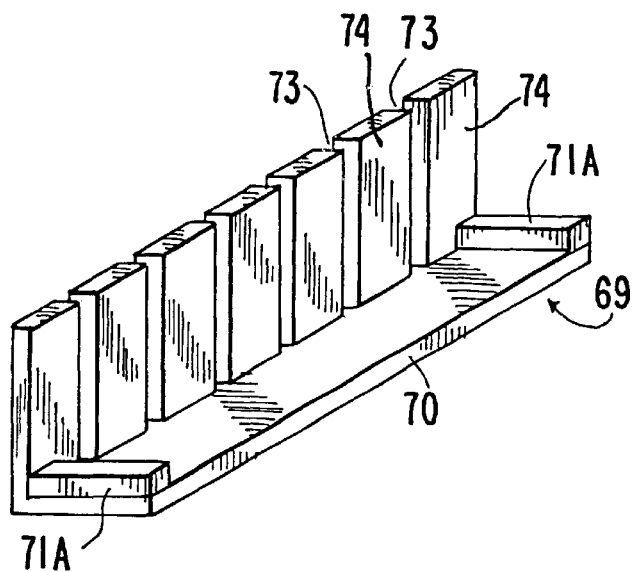
FIG. 14A is a perspective view of a flame shield fixture.
Figure 14B:
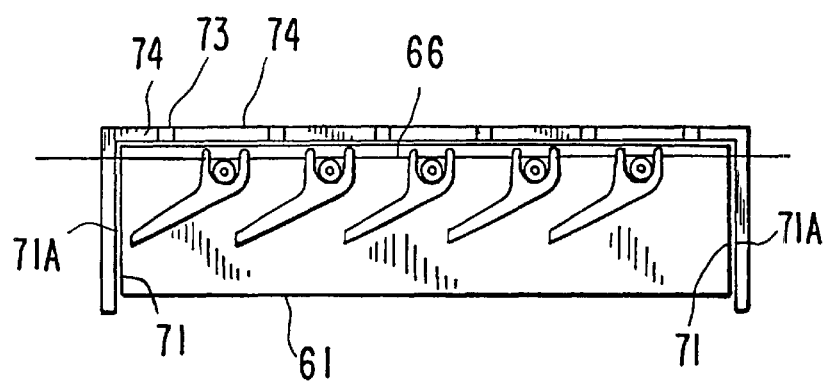
FIG. 14B is a fragmentary top plan view of the break-off fixture of FIG. 12 coupled to the flame shield fixture of 14A.

Next, as seen in FIGS. 11A, 14A and 14B, a transfer bar 67 with downward pins 68 is positioned essentially upside down with pins 68 loosely inserted into the apertures 63. Each transfer bar 67 has pins exactly corresponding to the ten posts 62 of the break-off fixture 60. The transfer bar sits in this position while the next burning phase occurs, however, the transfer bar could as well be utilized later, and its purpose will be explained later.

Figure 14C:
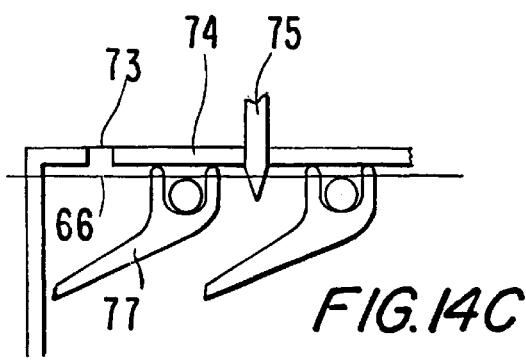
FIG. 14C is a fragmentary and enlarged view of FIG. 14B.

Next, as seen in FIGS. 14a, 14b the break-off fixture 60 loaded with flossers is placed onto a flame shield fixture 69 having a base 70, end guides 71A to receive and exactly position ends 71 of the break-off fixture so that the floss segments 66 will be directly adjacent the rectangular apertures 73 between each two adjacent vertical shields 74 as seen in FIGS. 14A–C.

Figure 14D:
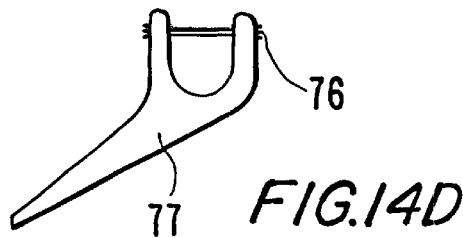
FIG. 14D is a fragmentary and enlarged top plan view of a finished flosser.
Figure 15A:
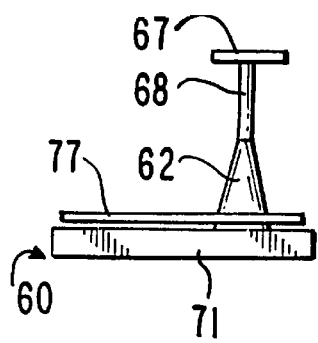
FIG. 15A is an end elevation view of the break-off fixture and transfer bar of FIG. 13B.
Figure 15C:
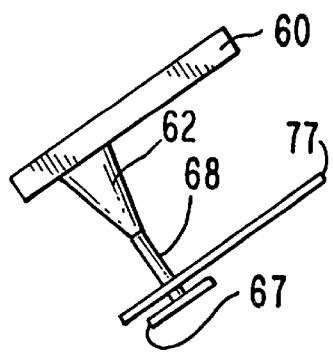
FIGS. 15B–15D are elevation views of the inversion of the structure of FIG. 15A.
Figure 15B:
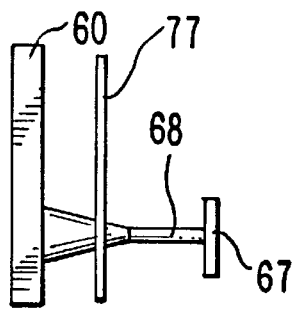
Figure 15D:
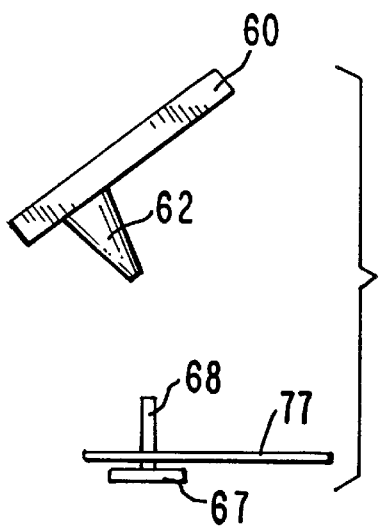

As seen in FIG. 14c, a blue flame 75 of propane gas is directed from top to bottom or bottom to top through each of said apertures 73 of approximately 3/16 inches in width to burn floss segments 66, thereby separating each all adjacent flossers. The flame melts the floss and cause the exposed ends of each multi-filament strand of ultra high molecular weight polyethylene floss to coalesce as seen in FIG. 14D into beads 76, each typically having a diameter greater than the original filament diameter. Consequently, the exposed end of the floss external of the arm of the flosser is greater in diameter than the original strand and thus greater in diameter than the aperture in the flosser arm through which the floss extends, and thus cannot be pulled through this aperture. Thus, the floss ends are secured from being pulled through the arms and out of the finished flosser 77, unless such excessive force is applied to break the floss or the floss holder.

The flame shields are made of steel or any flame resistant material that can tolerate this flame temperature for the few seconds or less it takes to burn the floss by directing the flame through the aperture. Obviously, the shields protect the plastic of the floss holder from being damaged or destroyed.

Figure 13A:
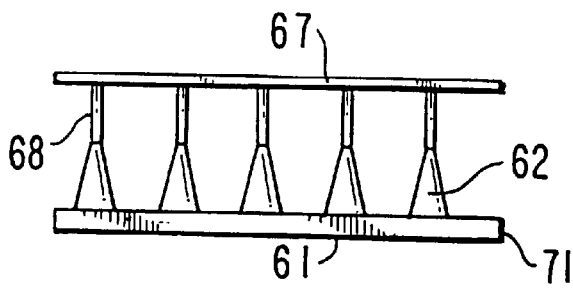
FIG. 13A is a front elevation view of the fixture of FIG. 11 with a transfer bar attached.
Figure 13B:
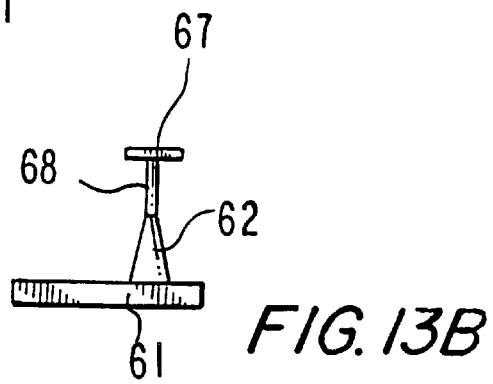
FIG. 13B is a side elevation view of FIG. 13A.

From this burning phase the flossers are severed from each other but still positioned closely adjacent to each other as they are still each straddling a post 63 of the break-off fixture coupled to the flame shield fixture. The next step is to separate the break-off fixture from the flame shield fixture and then to invert the break-off base 71, (with the transfer bar 67) (see FIGS. 13A, 13B) still loosely attached. The inversion is shown in FIGS. 15A–15D whereby the finished flossers each slide from a post 62 of the break-off base 71 onto a stem 68 of the transfer bar 67.

Figure 16:
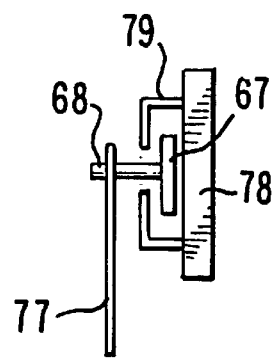
FIG. 16 is a side elevation view of an assembly fixture coupled to the transfer bar.

Now the slim and light-weight transfer bar and its stems hold the stacks of finished flossers which can be easily transported (and maintained in alignment) to a wall-mounted packaging fixture 78, as seen in FIG. 16, where brackets 79 receive the transfer bar 67. From this position and orientation the stems 67 extend generally horizontally and from them groups of flossers can be readily removed for subsequent packaging.

By using these break-off, flame shield and packaging fixtures the high-speed, high-volume process can be maintained. The flame shield fixture in particular allows three operations-in-one, namely, severing floss while protecting the holders from the flame and heat, fixing and securing the floss ends from pulling out of the holder, and setting-up the flossers for transfer.

Within the scope and spirit of this invention as defined by the claims, many variations are possible. The floss supply and magnetic tension mechanism may have alterations or substitutes; a great variety of injection molding machines may benefit from and use this invention; the take-off mechanism and the severing station, whether separate or combined may take many forms, in fact the take-off mechanism may even be a non-rotary device where successive shots are engaged, held and released within the concept of this invention.

What is claimed is:

1. In an injection molding machine operable with a mold, a supply of moldable plastic and at least one continuous strand of dental floss, successive portions of which strand are periodically directed to a location within said mold for each injection cycle thereof, whereby said injection molding machine produces successive shots, each shot including dental floss holders molded in situ onto said strand and where every two adjacent shots comprises a set of a first shot downstream of said mold, and a second shot downstream of said mold but upstream of said first shot with a segment of said strand extending between said shots, the improvement in combination therewith comprising first tensioning means upstream of said mold constantly applying tension to said strand in said upstream direction, take-off means comprising a first part for releasably engaging said first shot, a second part spaced from said first part for releasably engaging said second shot, and drive means periodically moving said first and second parts while they engage said first and second shots respectively away from said mold and periodically stopping said movement, thus applying and maintaining tension in said strand in said downstream direction, and severing means for severing said segment of said strand between said first and second shots while said second part temporarily maintains its engagement with said second shot.

2. Apparatus according to claim 1, wherein said drive means stops movement of said first and second parts while said injection molding machine operates its injection cycle, which includes closing said mold, injection of liquid plastic into the mold cavities, cooling and opening said mold and ejection of said shot.

3. Apparatus according to claim 1, wherein said mold is a multi-cavity mold having two lines of spaced-apart cavities, and said continuous strand of dental floss is designated the first strand, and said improvement comprises a second continuous strand of dental floss the same as and situated parallel and spaced from and operated similarly as said first continuous strand of dental floss and extends through said second line of said cavities.

4. In a multi-cavity injection molding machine including a body and operable with a supply of a continuous strand of dental floss, a set of mating mold pieces which when opened define between them cavities for a plurality of dental flossers and a predetermined floss space for a portion of said dental floss, and a supply of injection-molding plastic, said machine producing dental floss holders in successive shots spaced apart in the direction of downstream, every two adjacent shots of said successive shots comprising a set defining a first shot downstream of said mold and a second shot also downstream of the mold but upstream of said first shot, the improvement of comprising in combination, (a) a take-off means mounted to said body for engaging successive sets of shots, said take-off means comprising: a first part for releasably engaging said first shot, a second part spaced from said first part for releasably engaging said second shot, and drive means moving said first and second parts successively away from said mold pieces and thus applying tension in the downstream direction, (b) first tensioning means operative for constantly applying tension to said floss in the upstream direction, and (c) severing means for severing said first shot from said second shot while said second part maintains its engagement with said second shot, whereby said floss is maintained in tension before, during and after each injection cycle and as each of said first shots of each of said sets is severed from the adjacent second shot, the second shot to which it was engaged becomes anew first shot of the next successive set of shots.

5. Apparatus according to claim 4, wherein said machine when operated has a body and a top thereof and said floss space is oriented essentially vertically, and said take-off means comprises a wheel mounted rotatably on said body above said set of mold pieces, with said first and second parts circumferentially spaced apart on said wheel.

6. Apparatus according to claim 5, wherein said wheel has a central axis of rotation and said wheel is essentially hexagonal in cross-section perpendicular to said axis of rotation thus defining six sides, said wheel further comprising at least one projection extending generally radially outward from each of said six sides, each of said projections adapted to releasably engage one of said shots, during a portion of the wheel's rotation, whereby by rotation of said wheel one of said projections acts as said first part and another of said projections situated downstream of the wheel's direction of rotation acts as said second part.

7. Apparatus according to claim 4, wherein said floss defines a segment thereof which extends between each of said sets of successive shots, and said severing means comprises a torch whose flame is directed to and severs each of said segments of floss.

8. Apparatus according to claim 4, wherein said floss defines a segment thereof which extends between each of said sets of successive shots, and said severing means comprises a hot wire whose heat is directed to and severs each of said segments of floss.

9. Apparatus according to claim 4, wherein said floss defines a segment thereof which extends between each of said sets of successive shots, and said severing means comprises a knife whose edge is directed to and severs each of said segments of floss.

10. Apparatus according to claim 4, wherein said floss defines a segment thereof which extends between each of said sets of successive shots, and said severing means comprises a laser whose energy is directed to and severs each of said segments of floss.

11. Apparatus according to claim 6, wherein each of said shots comprises an array of dental floss holders with a central elongated runner of plastic extending in the downstream direction, a pair of strands of floss extending parallel to and spaced from said central runner, and a plurality of dental floss holders, each situated between and attached to said central runner and to one of said parallel strands of floss, with projection-engaging spaces defined between each two successive dental floss holders, and wherein each of said projections comprises a finger that projects into one of said projection engaging spaces and bears against one of said dental floss holders defining said space.

12. Apparatus according to claim 6, wherein said wheel sides are dimensioned so that each has length corresponding to the length of one of said shots and the segment of floss extending between two successive shots, whereby upon rotation of said wheel one of said shots is engaged by said first part of each of said sides of said wheel.

13. Apparatus according to claim 4, wherein floss from said supply of floss is directed to a location below said mold pieces before it enters said floss space between said mold pieces.

14. Apparatus according to claim 13, wherein said supply of floss further comprises first tensioning means applying a substantially constant minimum tension to said floss in the upstream direction toward said supply of floss.

15. Apparatus according to claim 4, wherein said take-up mechanism further comprises second tensioning means applying a substantially constant minimum tension to said floss in said downstream direction of said set of mold pieces.

16. Apparatus according to claim 14, wherein said tension applied by said first tensioning means is in the range of 5 to 10 psi.

17. In combination, the apparatus according claim 4 and a supply of injection molding plastic and a supply of dental floss, wherein said strand of dental floss is an ultra high molecular weight polyethylene having denier in the range of 400 to 700, and said injection-molding plastic is selected from the group consisting of polypropylene or polystyrene, nylon and ABS.

18. Apparatus according to claim 4, wherein said take-off means further comprises a chute having proximal and distal ends and an elongated body between said ends, wherein said proximal end receives said shots severed from adjacent upstream shots, said severed shots move along the length of said elongated body, and said distal end discharges said severed shots.

19. Apparatus according to claim 4, wherein said first tensioning means comprises:
   a cylindrical drum rotating in a first direction and feeding said floss in said downstream direction to said mold pieces, and
   a central rod about which said drum rotates, said central rod rotating in a direction opposite to that of said drum,
   said rod and drum further comprising magnetic means functioning as a slip clutch to restrain said rotation motion of said drum and thereby to apply said tension to said floss in said upstream direction.

20. Apparatus according to claim 19, further comprising means for adjusting the magnetic field and thereby adjusting the tension in said floss.

21. In combination, the apparatus according to claim 4 and a supply of injection molding plastic and a supply of dental floss, wherein the said supply of injection-molding plastic comprises polypropylene and said strand of dental floss comprises multifilament ultra high molecular weight polyethylene.

22. Apparatus according to claim 4, wherein said cycle of injection is about four to six shots per minute.

23. Apparatus according to claim 6, wherein said severing means comprise an electrically operated heating element mounted to each of said first parts of said wheel and situated to engage said segment of floss adjacent and upstream of each of said shots engaged by one of said first parts, and means for energizing said heat element to burn through said segment of floss after said next adjacent second part projection has engaged said next adjacent second shot upstream of said first shot.

24. Apparatus according to claim 23, wherein said heating element is a generally stiff wire extending transversely of the direction of said strand of floss.

25. Apparatus according to claim 23, further comprising timing means for activating said heat element with respect to a particular shot only when said wheel has rotated to at least 120° after said particular shot has been engaged by said wheel.

26. Apparatus according to claim 24, wherein said heat element is closely adjacent said projections.

27. In a method of making dental floss holders by an injection molding machine as defined in claim 1 where there is a mold having open and closed positions, and upstream of said mold is a supply of a continuous strand of dental floss, and said floss is directed to a position within said mold when said mold is in its open position, and said floss is molded in situ into said dental floss holders when said mold is in its closed position, the improvement of maintaining said floss in tension by applying a constant tension of at least 5 psi to said floss upstream of said mold and applying a constant tension of at least 5 psi to said floss downstream of said mold before, during and after each injection cycle.

28. A method according to claim 27, wherein said injection molding machine produces a continuous succession of shots, and each two successive shots comprises a set, one shot of said set being the downstream shot and the other being the upstream shot, and wherein said applying tension downstream of said mold comprises releasably engaging and applying said constant tension to said downstream shot of each of said sets while severing the floss between said shots of said set, and applying said constant tension to said upstream shot until it becomes the downstream shot of the next successive set of shots.

29. In an injection molding machine operable with a supply of a continuous strand of dental floss, a supply of injection-moldable plastic, and a multi-cavity mold having mating parts moveable between open and closed positions, with said dental floss extending from said supply through and out of said mold, said molding machine in operation producing a shot of a plurality of dental floss holders molded in situ onto said floss every injection cycle, where every two adjacent shots comprises a set with one of said set being the downstream shot and the other the upstream shot until the upstream shot becomes the downstream shot of the next adjacent shot, the improvement comprises (a) first tension means constantly applying a force to said floss upstream of said mold and in the upstream direction, (b) take-off means downstream of said mold engaged indirectly to said floss and maintaining tension in the downstream direction by intermittently pulling said floss in said downstream direction, after each injection and ejection phase and holding said floss from moving without pulling in any direction during said injection and ejection stage, and (c) severing means for severing the downstream shot from the upstream shot of each of said sets received by said take-off means while said upstream shot remains engaged to said take-off means and maintains said tension in said floss downstream of said mold.

30. Apparatus according to claim 29, wherein said first tension means is operable directly onto said supply of dental floss.

31. Apparatus according to claim 29, wherein said tension means is a magnetic clutch comprising first and second magnetic elements, one being a cylindrical drum from which said supply of floss unwinds, the second being a spindle about which said drum rotates in a first direction, said spindle rotating in a second direction opposite that of said drum thus applying a constant magnetic field force opposing said rotation of said drum and thus constantly applying a tension to said floss upstream of said mold in the upstream direction.

32. Apparatus according to claim 31, wherein said magnetic clutch applies a force which is adjustable in the range of 0.1 to 20 pounds (foot-pounds).

33. Apparatus according to claim 29, wherein said take-off means intermittently restrains said floss from moving in said upstream direction.

34. Apparatus according to claim 29, wherein said take-off means comprises an electric brake for said intermittent stopping and an electric clutch for restrain movement in said upstream direction.

35. Apparatus according to claim 34, wherein said electric clutch is automatically releasable to allow movement of said floss in the upstream direction only if the force on the floss in said upstream direction exceeds 10 pounds.

36. Apparatus according to claim 29, wherein tension in said floss upstream and downstream of said mold is maintained in the range of 5 to 10 pounds.

37. Apparatus according to claim 29, wherein mold opening defines a generally vertically oriented space with said upstream and downstream directions being below and above said mold respectively and said take-off means is situated above and thus downstream of said mold.

38. Apparatus according to claim 37, wherein said supply which is upstream of said mold directs said floss to enter said mold from below said mold.

39. Apparatus according to claim 29, wherein after each opening of the mold and ejection of a shot, said take-off means pulls said ejected shot and floss connected thereto downstream, with each successive two adjacent shots comprising a set of downstream and upstream shots.

* * * * *